United States Patent [19]

Matsuda

[11] 4,272,192
[45] Jun. 9, 1981

[54] HOLOGRAPHIC SHEARING INTERFERENCE CONTRAST METHOD AND INTERFEROMETER

[75] Inventor: Kiyofumi Matsuda, Musashi-Murayama, Japan

[73] Assignees: Agency of Industrial Science and Technology; Ministry of International Trade & Industry, both of Tokyo, Japan

[21] Appl. No.: 932,180

[22] Filed: Aug. 9, 1978

[30] Foreign Application Priority Data

Aug. 13, 1977 [JP] Japan .................................. 52/97227
Aug. 31, 1977 [JP] Japan .................................. 52/104645

[51] Int. Cl.$^3$ .................. G01B 9/02; G01B 9/021; G02B 5/32
[52] U.S. Cl. ...................... 356/347; 350/3.73; 356/353
[58] Field of Search ............ 356/347, 348, 353; 350/3.7, 3.73, 12, 13

[56] References Cited

U.S. PATENT DOCUMENTS

| | | | |
|---|---|---|---|
| 3,532,431 | 10/1970 | Bryngdahl | 356/347 |
| 3,572,934 | 3/1971 | Bryngdahl | 356/347 |
| 3,701,579 | 10/1972 | Zollner | 356/347 X |
| 4,118,124 | 10/1978 | Matsuda | 356/347 |

Primary Examiner—John K. Corbin
Assistant Examiner—Scott J. Sugarman
Attorney, Agent, or Firm—Kurt Kelman

[57] ABSTRACT

A transparent object can be converted into a visible image which is made up of a contrasted image of light and shade and therefore is readily perceivable with a three-dimensional illusion sensation by a method which comprises forming holograms with each of two collimated beams having slightly different angles of incidence and one reference beam, causing the reference beam to impinge upon the first hologram and thereby reproducing first order diffraction beams equivalent to the two collimated beams, then causing the reproduced diffraction beams to be passed through or reflected by the transparent object so as to impinge upon the second hologram and thereby reproducing diffraction beams laterally sheared and equivalent to the reference beam by which the second hologram was formed and imparting a suitable phase difference to these reproduced diffraction beams and thereby causing the beams to interfere with each other, whereby the phenomenon of interference thus produced on the surface of the object image gives rise to the visible image for desired observation.

9 Claims, 19 Drawing Figures

Fig_2

Fig_3

Fig_5

Fig_4(a)  Fig_4(b)

Fig_6(a)

Fig_6(b)

Fig_7

Fig_8

Fig.13 ated by angles of incidence of the two collimated planar beams and the distance, between the first hologram and the second hologram and are consequently allowed to interfere with each other. The amount of this shearing can be adjusted by suitably varying the distance between the two holograms. The conventional holographic interference method necessitates use of one new hologram for each observation because the observation inevitably requires the information on the wavefront of the particular object under observation to be recorded on that hologram. The interferometer designed and operated by method permits the desired observation to be obtained on a virtually limitless number of objects because it incorporates a set of two holograms as a component part thereof and obviates the necessity for photographing the holograms at the time of each observation. Further, this method has an advantage that since the desired observation of an object which either passes or reflects beam can easily be obtained by merely having the object placed in the path of the reference beam, the interferometer is capable of providing effective observation even for large objects.

HOLOGRAPHIC SHEARING INTERFERENCE CONTRAST METHOD AND INTERFEROMETER

BACKGROUND OF THE INVENTION

This invention relates to a holographic shearing interference contrast method for the observation of a transparent object or phase object.

When a light passes through a phase object (hereinafter referred to merely as "object") which absorbs light, the light wave loses intensity. Since human eyes and photosensitive films are sensitive to such a variation in the light intensity, the image of such an object can be observed or recorded through an ordinary optical microscope. In the case of a perfectly transparent object, however, the image of the object cannot be observed through an ordinary optical microscope because the object does not absorb light. Whenever a light passes through any object, there is produced a lag in phase. To permit the observation of the object, therefore it becomes necessary for the phase difference of light to be converted into corresponding difference in intensity. One of the methods which are available for the purpose of this conversion is the phase contrast method which is employed such as in conventional phase contrast microscopes. According to this method, a diffraction beam which has passed through a given object and a beam which has advanced without passing through any obstacle are passed through a transparent object to give rise to a phase difference of $\pi/2$, namely, a contrast is given to the image of the article in proportion to the index of refraction of the transparent object.

The shearing interference method is also available for the aforementioned conversion. This method enables a transparent object to be observed in a shape made up of interference fringes. The shearing interference contrast method is the product of the combination of this shearing interference method and the aforementioned contrast method. Unlike the shearing interference method which resorts to observation of a shape made of several interference fringes rather difficult of discernment, the shearing interference contrast method enables the image of the object itself to be observed by virtue of variation in the light intensity instead of the shape made up of interference fringes. It is also capable of allowing observation of a slight variation in the index of refraction even smaller than the wavelength of light. This method obviates the necessity for a phase plate and other similar accessorial means.

The shearing interference contrast method accomplishes the desired observation of a given object by dividing the wavefront issuing from the object into two portions (amplitude division), shearing the divided wavefronts laterally, causing the two wavefronts to interfere with each other by giving them a phase difference equivalent to one fourth of the wavelength ($\pi/2$) and converting the variation in phase into a corresponding variation in light intensity. By this method, since the wavefront issuing from the object is divided into two portions and the phase between these two wavefronts is continuously varied, the image of this object can be observed in the form of the light and dark image obtained when a light diagonally impinges upon an uneven object. So far as a given object has its phase varied as described above or, in the absence of an uneven surface, has its index of refraction varied similarly, the image of the object can be observed in the form of light and shade so as to produce a three-dimensional illusion on the part of the observer.

Formerly the inventor suggested an interferometer which operates by the application of holograms to the shearing interference method ("Holographic shearing interferometer": U.S. Pat. No. 4,118,124, dated Oct. 3, 1978. The interferometer uses a set of two holograms each produced by the interference fringes due to two collimated planar beams having slightly different angles of incidence and one reference beam. These two holograms are set in position and the beam which has passed through a given object or has been reflected by the object is caused to impinge upon the first hologram as a reference light. Behind the first hologram, there are obtained two first order diffraction beams equivalent to the two collimated planar beams which have served the purpose of forming interference fringes on the first hologram. At this time, the two diffraction beams of the first hologram impinge at different positions on the object to cause object beams. This means that the diffraction beams are sheared by this difference in position. When the two object beams impinge upon the second hologram, they reproduce one first-order diffraction beam traveling in the same direction as the reference beam and give rise to interference fringes behind the second hologram. These are shearing interference fringes which occur when the wavefronts of a given object are laterally sheared by an amount to be determined An object of this invention is to provide, through application of the holographic shearing interference method to the shearing interference contrast method, a shearing interference contrast method using holograms which, unlike the conventional contrast method which suffers from various disadvantages such as poor feasibility of manufacture, limited capacity of observation, mechanical instability and difficult adjustment, enjoys many advantages such as high resolving power, notable stability to withstand vibrations and other external impacts, wide field of observation, ease of adjustment and ability to provide heretofore unattainable quantitative measurement.

Another object of this invention is to provide an interferometer or interference microscope adapted for the holographic shearing interference contrast method mentioned above.

SUMMARY OF THE INVENTION

To accomplish the objects described above according to the present invention, there is provided a holographic interference contrast method which, by use of an apparatus comprising a first hologram adapted to have recorded thereon through double exposure the interference fringes resulting from the interaction between each of two collimated planar beams having slightly different angles of incidence and one reference beam and a second hologram positioned in the image plane of the first hologram and adapted to have recorded thereon through the medium of the image-forming system the interference fringes resulting from the interaction between the first order diffraction beams reproduced by illumination of the first hologram with the reference light and another reference light, effects desired observation of a given object by exposing the first hologram to an illumination beam introduced in the same direction as the reference beam and thereby allowing two resultingly reproduced first order diffraction beams equivalent to the collimated planar beams of incidence to impinge upon the object under observation, and then causing two object beams which occur when the object passes or reflects the first order diffraction beam to impinge upon the second hologram and thereby allowing the two object beams to propagate in the same direction as the reference beam of the second hologram and, at the same time, laterally moving slightly the second hologram for thereby having the two object beams give rise to a phase difference of $\pi/2$ and interfere with each other, whereby on the image plane, the phase object forms an image which is made up of a converted image of opposite gradients into lighter or darker intensities in comparison to the background and, therefore, is perceived with a three-dimensional illusion.

The two holograms are not used for photographic recording of a given object but are used as a component element of a system designed for observation of a transparent object. Thus, the present invention obviates the necessity for preparing a new hologram each time there is given an object for observation. Further, the phase image of a given object can be formed behind the second hologram by merely having the two holograms located at prescribed positions and the object placed behind the first hologram. Thus, the observation of the object can easily be carried out. This method can easily be adapted for optical devices such as interferometers and microscopes to afford systems which enjoy high resolving power and stable performance.

The other objects and characteristic features of the present invention will become apparent from the description to be given in further detail hereinafter with reference to the accompanying drawing.

BRIEF EXPLANATION OF THE DRAWING:

FIGS. 1(a) to 1(d) are explanatory diagrams of the phase contrast method resorting to shearing interference;

FIG. 1(a) showing the phase distribution of the phase object,

FIG. 1(b) showing the phase distributions of the phase object as divided in two and sheared laterally, FIG. 1(c) showing the distribution of interference fringes relative to the variation in phase and FIG. 1(d) showing the distribution of the intensity of the phase object under observation.

FIGS. 2 and 3 are schematic diagrams illustrating the preparation of holograms to be used in the holographic shearing contrast interference method of the present invention.

FIGS. 4(a) and 4(b) are schematic diagrams illustrating the first preferred embodiment of the interference method of this invention.

FIG. 5 is a schematic diagram illustrating a phase difference imparted to the object beams.

FIG. 6(a) is a photograph of the pattern of interference obtained of a phase object by the holographic shearing contrast interferometer according to the present invention.

FIG. 6(b) is a photograph of the pattern of interference obtained of a phase object by the conventional (Mach Zehnder) interferometer.

FIGS. 7 and 8 are schematic diagrams illustrating the second preferred embodiment of the interference method of this invention.

FIGS. 9(a) and 9(b) are schematic explanatory diagrams of the third preferred embodiment of the interference method of this invention as applied to a reflection type microscope.

FIG. 10 is a schematic explanatory diagram of the third preferred embodiment of FIGS. 9(a) and 9(b), as applied to a reflection type microscope.

FIG. 11 is a schematic diagram illustrating the fourth preferred embodiment of the interference method of this invention.

FIG. 12 is a schematic diagram illustrating the operating principle of the fourth preferred embodiment of this invention of FIG. 11.

DESCRIPTION OF THE PREFERRED EMBODIMENTS

The shearing interference contrast method is extensively used for the observation of live cells and the observation of transparent substances such as crystals and fibers. Such a transparent object as fails to show contrast of light and shade (hereinafter referred to as "object") cannot be analyzed for its minute structure by unaided eyes or with the aid of photography. Thus, the shearing interference contrast method obtains desired observation by dividing the wavefront passed or reflected by the object in two (amplitude division), laterally shearing the two wavefronts relative to each other and thereby causing the two divided wavefronts to give rise to a phase difference and interfere with each other and converting this phase difference into a corresponding variation in the intensity of light. The operating principle is described with reference to FIGS. 1(a) to 1(d).

FIG. 1(a) depicts an object beam $\Sigma$ obtained by passage of beam through a simple rectangular object having a phase height $\Delta$. When this object beam $\Sigma$ is divided into two object beams $\Sigma_1$ and $\Sigma_2$ and the two object beams are laterally sheared relative to each other by an amount of $\phi$ and further give rise to a phase difference $\delta$ of $\pi/2$ therebetween, the outcome will be as shown in FIG. 1(b). When the object beams $\Sigma_1$ and $\Sigma_2$ are caused to interfere with each other and the phase between these two object beams is continuously varied, the intensity of light is varied in the pattern of a cosine wave as shown in FIG. 1(c). Let $\delta$ stand for the phase difference between the two object beams $\Sigma_1$ and $\Sigma_2$, and in the diagram of FIG. 1(b), $\delta=\pi/2$ is satisfied when $y<y_1$, $\delta=\pi/2 + \Delta$ is satisfied when $y_1 \leq y \leq y_2$, $\delta=\pi/2$ is satisfied when $y_2<y<y_3$ and $\delta=\pi/2 - \Delta$ is satisfied when $y_3 \leq y \leq y_4$ respectively. The distribution of the light intensity brought about by the interference between $\Sigma_1$ and $\Sigma_2$ can be determined from FIG. 1(c) as shown in FIG. 1(d). As is clear from this diagram, there is consequently obtained an image formed of light and dark of varying intensity $\tau$ in much the same way as obtained by exposing the rectangular object of FIG. 1(a) to a light projected diagonally from the right upper side.

This invention carried out the shearing interference contrast method by using holograms. As a result, desired observation of transparent objects can be obtained easily and stably. Now, the holographic shearing interference contrast method of this invention will be described.

In the present invention, the first hologram $H_1$ $R_1$ is produced in such a way that a photographic plate 1 is exposed to a reference beam $R_1$ and a collimated planar beam $A_1$ to cause a fringe pattern of the interference between the beams $R_1$ and $A_1$ to be recorded thereon and further exposed to the reference beam $R_1$ and another collimated planar beam $A_2$ to cause a fringe pattern of the interference between the beams $R_1$ and $A_2$ to be doubly recorded upon the fringe pattern of the interference between the beams $R_1$ and $A_1$ which was in advance recorded on the plate. In FIG. 2, the two collimated planar beams $A_1$, $A_2$ share the y-axis passing the origin o over the photographic plate and have slightly different angles of incidence so as to produce an angle $\theta$ therebetween, and the reference beam $R_1$ passes the x-axis drawn through the origin o and forms a slight angle $\rho$ of incidence relative to the vertical line drawn through the origin. The three beams coincide with one another on the surface of the photographic plate 1 to form a hologram.

The second hologram is obtained similarly to the first hologram. More specifically, the second hologram $H_2$ is obtained, as shown in FIG. 3, by causing the reference beam $R_1$ to impinge upon the first hologram produced as described above and thereby giving rise to first order diffraction beams $a_1$, $a_2$ equivalent to the collimated planar beams $A_1$, $A_2$ of incident mentioned above, thereafter allowing the diffraction beams to be passed through a pair of collimator lenses $L_1$, $L_2$ so as to form an image on the surface of the photographic plate 2, and causing a reference beam $R_2$ equivalent to the reference beam $R_1$ used for the first hologram to impinge upon the image mentioned above. The component elements which are required for the formation of the second hologram are disposed, as illustrated, at a distance equal to common focal length f of the pair of lenses $L_1$, $L_2$. A pinhole P is placed at the middle point on the focal plane of lens $L_1$ between the lenses $L_1$, $L_2$ serves the purpose of eliminating from the first hologram reproduced diffraction noise components such as zero order, 2nd order and higher order diffraction beams which result from the nonlinear of a photographic plate.

Now, the application of the pair of holograms obtained as described above to the holographic shearing interference contrast method of this invention will be described with reference to FIG. 4.

The two holograms $H_1$, $H_2$ and the collimator lenses $L_1$, $L_2$ and disposed in the same positional relationship as in the formation of the second hologram and arranged so that the holograms will fall at the focal distances of the respective lenses. In this arrangement, when the reference beam $R_1$ is caused to impinge upon the first hologram, there are produced first order diffraction beams $a_1$, $a_2$, which are passed through the collimator lenses to form an image on the second hologram as shown in FIG. 4(a). When the two diffraction beams $a_1$, $a_2$ impinge upon the second hologram, there is consequently reproduced a first order diffraction beam $a_2$ equivalent to the reference beam $R_2$ behind the second hologram. When a transparent object O is placed between the first hologram and the first collimator lens $L_1$ in this arrangement, the object beam which has passed the object possesses a phase variation due to the index of refraction peculiar to the particular object under observation. The object beams $\Sigma_1$, $\Sigma_2$ thus possessing a phase variation interact to reproduce a common first order diffraction beam $a_3$ behind the second hologram. When at this point, the second hologram is slightly moved by a suitable amount $\phi$ (as mentioned below) in the direction of the y-axis as shown in FIG. 4(b), a phase difference of $\pi/2$ can be imparted between the two object beams $\Sigma_1$, $\Sigma_2$. When this phase difference is formed on the plane of observation 3, the variation in refractive index peculiar to the object under observation can be converted into a corresponding variation of intensity by virtue of the phenomenon of interference, giving rise to an optical image I produced in the form of a shadow image productive of a three-dimensional illusion. This interference image I is substantially the same as the image which is obtained by an ordinary phase-contrast microscope. The plane of observation 3 may be in the form of a projection screen or a photographic film. Otherwise, the image thus formed may be transferred as an input into a proper electronic memory element through the medium of an electronic screen made up of a photoelectric sensor and a buffer or reproduced in the form of a TV image for direct visual observation. In the present preferred embodiment, there is incorporated a sliding mechanism 11 which serves to permit fine movement of the second hologram. This mechanism has a construction similar to that of any ordinary micrometer, so that a simple rotation imparts a sliding movement to the thimble.

The lens $L_3$ fulfills a dual role of observing the image of the object and converging the beams on the focal plane so as to permit elimination of undesirable order diffraction noise components. The plane of observation 3 is desired to be located behind the lens $L_3$ such as of a camera at a distance two times the focal length of the lens. The pinhole P is placed in the focal plane of the lens $L_3$ and used for the purpose of eliminating diffraction noises. The image I' indicated by dotted lines between the second hologram $H_2$ and the lens $L_3$ is an object image reproduced by the second hologram. This image is rendered visible by means of a screen placed in this position. The lens $L_3$ may be a camera lens, for example, which serves the purpose of forming a real image I on the plane of observation 3 such as a photographic plate disposed behind the lens $L_3$ at a distance two times the focal length of the lens.

The phase difference imparted to the object beams by a fine movement of the second hologram in the direction of the y-axis will be described with reference to FIG. 5. The two divided first order diffraction beam of the first hologram are passed through the object to give rise to object beams $\Sigma_1$, $\Sigma_2$ and the two object beams are matched on the second hologram. In the diagram, however, the two object beams are each divided in two to facilitate comprehension.

The phase difference of $\pi/2$ between the two wavefronts $\Sigma_1$, $\Sigma_2$ is produced by moving the second hologram $H_2$ by an amount equivalent to half the period of the interference fringes which result from the interaction between the two light beams $\Sigma_1$ and $\Sigma_2$. The marks o and • used in FIG. 5 represent the positions of the maximum and minimum intensities respectively in the interference fringes. Now, as the second hologram $H_2$ is moved by the amount of $\pi/2$ along the y-axis, the positions $E_1$ of maximum intensities of interference fringes recorded on the second hologram $H_2$ shift to the positions $E_2$ which were assumed by the minimum intensities before the movement. As shown in FIG. 5, the movement of the second hologram $H_2$ gives rise to no phase retardation in the object beam $\Sigma_1$. In the object beam $\Sigma_2$, however, there occurs a phase retardation because the wavefront through $E_1$ is converted to the wavefront through $E_2$. The amount of this phase retardation is $\pi/2$, as shown in the figure. It is consequently found that a slight movement of the second hologram $H_2$ along the y-axis produces the phase difference ($e_1$ or $e_2$) of $\pi/2$.

FIG. 6(a) is a photograph showing a transparent phase object visually reproduced by the interference method of the present invention. The model object involved here is a transparent object incorporating annular portions concentrically raised thereon. When the same object is observed with the Mach-Zehnder interferometer, one of the interferometers operated by the conventional shearing interference contrast method, there is obtained a pattern as shown in the photograph of FIG. 6(b).

The interference method of the present invention enables a transparent object heretofore considered to be unobservable by the conventional method to be visibly reproduced with a high resolving power. Furthermore, the condition of the dark portions of the reproduced object can easily varied by suitably adjusting the amount of shearing of the second hologram in accordance with the contrast between microscopic concavities and convexities of the phase object and the variation in the density of microscopic structure of the object.

Another preferred embodiment of the present invention represents a modification to the aforementioned method of FIG. 4 wherein the second hologram $H_2$ is adapted to be sheared only along the y-axis so as to produce dark only in one direction of the object; the modification being such that such dark can be imparted in two vertically intersecting directions of the y-axis and x-axis (two-dimentionally). By this modified method, one of the two collimated planar beams used in the former preferred embodiment is replaced by a spherical wave beam; the holograms are obtained by using one planar wave beam and one spherical wave beam. As illustrated in FIG. 7, the spherical wave beam $A_1$ and the planar wave beam $A_2$ assume beam paths vertically incident to the surface of the photographic plate 1 and the reference beam $R_1$, similarly to the reference beam involved in the former preferred embodiment, impinges upon the plate at a slight angle relative to the vertical line drawn to the plate. By causing the reference beam $R_1$ to impinge upon the first hologram $H_1$ formed as described above, there are reproduced two diffraction beams $a_1$, $a_2$, which are passed through a pair of collimator lenses $L_1$, $L_2$ so as to form an image on the second photographic plate 2. Then the second hologram $H_2$ is obtained by causing the reference beam $R_2$ to impinge upon the image.

The construction which is required for the observation of a transparent object by use of the two holograms produced as described above is similar to that of the first preferred embodiment as illustrated in FIG. 8. The only difference is that when the reference beam $R_1$ is caused to impinge upon the first hologram $H_1$, diffraction beams $a_1$, $a_2$ equivalent to the spherical wave beam $A_1$ and the planar wave beam $A_2$ of FIG. 7 are reproduced along the same optical axis behind the first hologram. This means that since the diffraction noises which are generated by the respective holograms at the time the first order diffraction beam $a_3$ of the second hologram is converged by the collimator lens $L_3$, are also focused on the same optical axis as the necessary diffraction beam $a_3$, required adjustment of the pinhole P for the elimination of noises can be obtained by a simple operation of moving the pinhole along the optical axis. A conspicuous effect to be brought about by this construction is the fact that the second hologram is capable of two-dimensional lateral movement in the x-axis and y-axis, whereas the second hologram of the first preferred embodiment (FIGS. 4 and 5) is only capable of one-dimensional lateral movement in the y-axis. This preferred embodiment, therefore, has an advantage that since the reproduced diffraction beams $a_1$, $a_2$ assume one and the same optical axis, the results are the same when the lateral movement of the second hologram is effected in one direction or in the other.

The preferred embodiments given to this point have been invariably described as ones adapted for use with penetration type microscopes. As illustrated in FIGS. 9(a) and 9(b), the method of this invention can also be applied to a reflection type microscope. The reflection type microscope using this method can be adapted for surface observations of opaque reflective phase substances such as metals and non-metals as well as for biological studies. The object O shown in FIGS. 9(a) and 9(b) is also one of the reflective materials. In this preferred embodiment, the white light from a mercury vapor bulb 5 is used as the light source for the reproduction of holograms. This white light is converged by a condenser lens 6 and then corrected into a collimated planar beam by a collimator lens 7 so as to be used as the reference beam $R_1$ for the first hologram $H_1$. Consequently, the first hologram $H_1$ reproduces two first order diffraction beams $a_1$, $a_2$ behind it. The first order diffraction beams $a_1$, $a_2$, after having their paths bent by a half mirror 8, are directed to the objective lens 9 of a microscope. The object lens 9 converts the diffraction beams into a collimated light beam and directs the light beam onto the surface of the object O. Upon reaching the object, the collimated light flux is reflected by the surface of the object. At this point, the light beam acquires a phase difference corresponding to surface conditions of the object such as microscopic concavities and convexities. The reflected object beam which has acquired the phase difference returns along the path of incident beam with axial symmetry, passes the objective lens 9 and advances straight to the half mirror 9. The reflected object beam which has passed through the collimator lens $L_2$ is matched on the surface of the second hologram $H_2$, with the result that a diffraction beam equivalent to the second reference beam is reproduced behind the second hologram $H_2$. Direct ocular observation of this reproduced diffraction beam through the eyepiece (not shown) permits the observer to perceive the object in the form of an aggregate of interference fringes arranged in accordance with the phase difference of the surface of the object under observation. In the case of an object whose phase variation is small for the wavelength of light or an object involving a complicated phase variation, ocular observation of a contrasted image providing a good three-dimensional illusion brings about the same results as those obtained with the first preferred embodiment of FIGS. 4 and 5. The pinholes $P_1$, $P_2$ used in this microscope have the same function as that of the pinhole involved in the first preferred embodiment. FIG. 10 is a schematic design drawing of a holographic shearing interference microscope actually constructed personally by the inventor by the application of the method of this invention to an ordinary microscope. In the drawing, M stands for a reflector (mirror) and the other symbols are like those used in the preceding preferred embodiments for denoting like means.

According to the present invention, an interferometer of a simple construction using two holograms can easily be adapted for use with an interference microscope, the adjustment of the amount of shearing can be effected suitably in accordance with the condition of the particular object under observation, the light source may be either the white light from a mercury vapor bulb or a laser beam, the observation is not affected by the lack of homogeneity of emulsion used in the photographic plate or by lens aberration. These form a part of many advantages offered by the present invention. The preferred embodiments described up to this point have necessitated use of two holograms. By the following modification to the method of this invention, however, the same results can be obtained by use of only one hologram.

The sole hologram H which is involved in this fourth preferred embodiment of this invention is obtained in the same way as the first hologram $H_1$ of the foregoing preferred embodiments. Since there is no need for any second hologram, this preferred embodiment obviates the necessity for the adjustment involved in setting two holograms at prescribed positions prior to the formation of the holograms. The principle by which an interference image of the portion of the object O under observation is obtained by means of one hologram will be described with reference to FIG. 11. When the reference beam R is caused to impinge upon the hologram H obtained by the method of FIG. 2, two diffraction beams $a_1$, $a_2$ are reproduced behind the hologram. The reproduced diffraction beams $a_1$, $a_2$ are passed by the objective lens 9 but are reflected by the object O. When the incident beam reaching the object has a path perpendicular to the surface of the object, the reflected object beams $\Sigma_1$, $\Sigma_2$ are returned along the optical path of the incident beam with axial symmetry and allowed to impinge upon the hologram H. Consequently, the hologram reproduces a first order diffraction beam $a_3$ containing the information on the phase difference of the two reflected object beams $\Sigma_1$, $\Sigma_2$ in the same direction as that of the reference beam R.

In the present preferred embodiment, movement of the hologram H does not bring about any shearing. This is because equivalent diffraction beams are reproduced in the same direction as the reference beam no matter what part of the surface of hologram the irradiation beam may be allowed to hit, unless the angle formed between the hologram and the irradiation beam (the reflected object beam from the object in this particular case) is varied. A variation produced in the path of beam by oblique displacement of the object O means, in effect, the fact that the reflected object beams $\Sigma_1$ and $\Sigma_2$ are laterally shifted. This means that a phase difference $\pi/2$ can be imparted to the object's wavefronts by suitably adjusting the oblique displacement $\psi$. The principle of this operation will be described with reference to FIG. 12. The dotted lines in this diagram show the state assumed before the lateral movement. Thus when the first order diffraction beam $a_1$ (not shown) of the hologram H has a path perpendicular to the surface of the object O under observation, the incident path and the reflected path are identical so that the reflected light returns to the hologram and forms a first interference figure behind the hologram (left upper part in the diagram). To impart some contrast to this interference figure, the object O is inclined by an angle $\psi$ in the second stage. Consequently, the diffraction light $a_1$ as an incident light impinges upon the object O and is reflected thereby by an angle of $2\psi$. When this reflected light impinges upon the hologram again, the position of this impingement is laterally deviated from the position of the first impingement. The amount of this lateral movement (deviation) is variable with the angle of incidence of the diffraction beam $a_1$ relative to the object and the angle of inclination $\psi$ of the object. Since the diffraction beams $a_1$ and $a_2$ thus have different angles of incidence relative to the object, the amounts of movement at the time of the impingement upon the hologram H are different. This difference in the amount of movement gives rise to a phase difference between the object beams $\Sigma_1$ and $\Sigma_2$ which are again diffracted by the hologram H. Thus, a phase difference of $\pi/2$ can be imparted by suitably selecting the angle of inclination $\psi$ of the object. Consequently, the reflected object beams $\Sigma_1$ and $\Sigma_2$ are caused to interfere with each other. This phenomenon of interference permits the object to be visibly observed in image the form of an image which is made up of light and dark and consequently perceived with a clear three-dimensional illusion.

Figure 13:
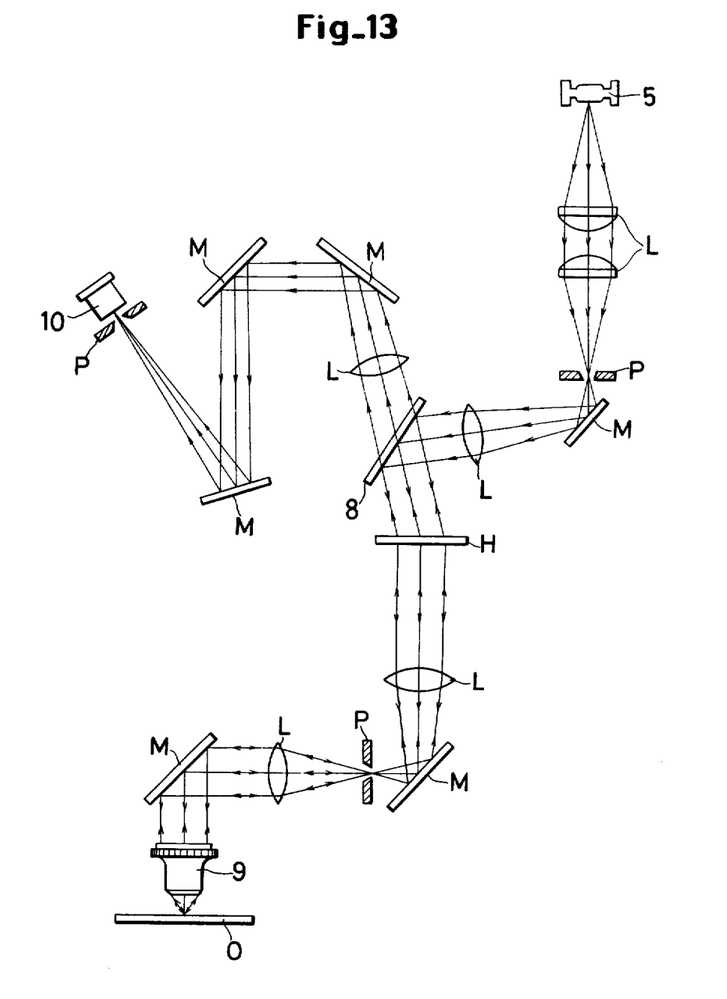
FIG. 13 is a schematic explanatory diagram of the fourth preferred embodiment of this invention as applied to a reflection type microscope.

FIG. 13 depicts application to a microscope of the interference method of this invention involving use of one hologram. In the diagram, L stands for a Lens, M for a reflector, P for a pinhole filter and 10 for an eyepiece and the other symbols are like those used in the other preferred embodiments for denoting like means.

Although a monochromic coherent beam such as a laser beam is desirably used, the present preferred embodiment is illustrated as involving use of a super high pressure mercury vapor bulb or iodine vapor lamp. The beam issuing from the light source has its path directed by the lens, pinhole, reflector, etc. and then bent by the half mirror 8 and caused to iminge upon the hologram H as a reference beam. Consequently, the hologram H reproduces diffraction beams behind it. The reproduced diffraction beams are directed to the objective lens 9 through the medium of the lens, reflector, pinhole, etc. In this microscope, the path from the hologram H to the objective lens 9 is equivalent to that of FIG. 12. The behavior of the beams from the time they are reflected by the object O to the time they are returned to the hologram H is the same as already described. By the reflected beams from the object, the diffraction beams reproduced by the hologram are caused to advance straight to the half mirror 8 and to the eyepiece through the medium of the lens, reflector, etc. to form a visible image.

In the manner described above, the surface of the object under observation can be reproduced in the form of a visual image with good a three-dimensional illusion. The multiplicity of lenses, reflectors and pinholes used in the microscope of the present preferred embodiment are disposed as illustrated for the purpose of precluding possible lens aberration and noises and heightening the accuracy of beam paths. The construction is not different from that which is frequently observed in ordinary interference microscopes.

According to the present invention, an interferometer can be constructed by using one or two holograms and it can be operated to provide easy and prompt observation of cellular tissues of living organisms and crystal growth and the lattice condition of transparent solid substances which generally defy observations by unaided eyes or with the aid of photography. By the treatment of shearing effected by means of holograms or through displacement of the object under observation, the interference image under observation can be given a three-dimensional depth to ensure ease of observation. To cite characteristic features of the present invention, the interferometer involves use of a common beam path and, therefore, enjoys mechanical stability in the face of vibration and turbulence of ambient air; it is capable of providing effective observation of even large objects; it permits observation simultaneously with quantitative measurement; it permits the amount of shearing to be adjusted freely in proportion to the phase difference of the object; it obviates the necessity for incorporating high-performance optical elements; it tolerates poor accuracy of planar beams; it is not affected at all by the absence of homogeneity of emulsion used in the photographic plate; it enjoys high resolving power; it can be effectively operated with semimonochromic light or white light as the light source besides a monochromic light such as the laser beam; and it can be applied to ordinary interference optical systems other than interference microscopes.

What is claimed is:

1. A holographic shearing interference contrast method which comprises:
   producing a first hologram by using interference fringes resulting from the interaction between a first reference beam and each of two incident beams having slightly different angles of incidence, and a second hologram by using interference fringes resulting from the interaction between a second reference beam and each of first order diffraction beams reproduced by illumination of the first hologram with a beam equivalent to the first reference beam;
   placing a transparent phase object under observation between said first and second holograms arranged in the same positional relationship as in the producing of the holograms;
   impinging upon said second hologram the first order diffraction beams reproduced by illumination of said first hologram with said beam equivalent to the first reference beam and passed through said object for thereby reproducing a first order diffraction beam of the second hologram; and
   imparting a phase difference to said first order diffraction beam of the second hologram by laterally moving said second hologram a small displacement so as to provide a visible image having a three-dimensional illusion on an observation plane.

2. A holographic shearing interference contrast method which comprises:
   producing a first hologram by using interference fringes resulting from the interaction between a first reference beam and each of two incident beams having slightly different angles of incidence, and a second hologram by using interference fringes resulting from the interaction between a second reference beam and each of first order diffraction beams reproduced by illumination of the first hologram with a beam equivalent to the first reference beam;
   placing between said holograms a half mirror adapted to bend the optical axes of the first order diffraction beams of the first hologram;
   locating a reflective phase object under observation in such a manner that object beams deflected by the surface of the object return along the paths of the first order diffraction beams, deviated by the half mirror and directed onto the surface of the object;
   impinging upon the second hologram the object beams deflected on the surface of the object to reproduce a first order diffraction beam of the second hologram; and
   imparting a phase difference to the reproduced first order diffraction beam of the second hologram, so as to produce a visible image having a three-dimensional illusion by virtue of the phenomenon of interference on an observation plane.

3. A holographic shearing interference contrast method according to claim 2, wherein the second hologram is moved slightly laterally to impart a phase difference to the reproduced first order diffraction beam of the second hologram.

4. A holographic shearing interference contrast method according to claim 2, wherein the reflective phase object under observation is slightly inclined to impart a phase difference to the reproduced first order diffraction beam of the second hologram.

5. A holographic shearing interference contrast method which comprises:
   producing a hologram by using interference fringes resulting from the interaction between a reference beam and each of two incident beams having slightly different angles of incidence;
   locating a reflective phase object under observation behind said hologram;
   directing first order diffraction beams reproduced by illumination of the hologram with a beam equivalent to the reference beam to the surface of the object to produce object beams reflected by the object;
   reproducing another first order diffraction beam in the same direction as that of the reference beam by directing the reflected object beams to the hologram; and producing a variation in the path of the reflected object beam by oblique displacement of the object so as to laterally shift the reflected object beams to as to impart a phase difference to said another first order diffraction beam reproduced by illumination of the hologram with the reflected object beam;
   whereby a visible image having a three-dimensional illusion is produced on an observation plane.

6. A holographic shearing contrast interferometer which comprises:
   a first hologram produced by using interference fringes resulting from the interaction between a first reference beam and each of two incident beams having slightly different angles of incidence;

at least a pair of first and second collimator lenses arranged behind said first hologram so as to allow the first order diffraction beams to be passed therethrough to form an image on the focal plane of the second collimator lens;

a second hologram located on the focal plane of the second collimator lens and produced by using the interference fringes resulting from the interaction between a second reference beam and each of the first order diffraction beams which are reproduced by illumination of the first hologram with a beam equivalent to the first reference beam and passed through the collimator lenses;

a sliding motion mechanism serving to permit fine movement of the second hologram;

at least a third collimator lens located behind the second hologram; and an observation plane located behind the third collimator lens;

whereby when a transparent phase object is placed behind the first hologram, desired observation is accomplished by causing the object beams, produced by passing the first order diffraction beams through the object, to be directed to the second hologram for reproducing the first order diffraction beam of the second hologram, slightly moving the second hologram laterally by means of the sliding motion mechanism to impart a phase difference to the reproduced first order diffraction beam of the second hologram and thereby providing a visible image having a three-dimensional illusion on the observation plane.

7. A holographic shearing contrast interferometer according to claim 6, wherein a pinhole filter for eliminating diffraction noises is disposed in the focal plane of the third collimator lens.

8. A holographic shearing contrast interferometer which comprises:

a first hologram produced by using interference fringes resulting from the interaction between a first reference beam and each of two incident beams having slightly different angles of incidence;

at least a pair of first and second collimator lenses arranged behind said first hologram;

a half mirror disposed between said collimator lenses and adapted to bend the optical axes of the first order diffraction beams reproduced by illumination of the first hologram with a beam equivalent to the first reference beam;

an object lens for allowing the first order diffraction beams deviated by the half mirror and the object beams produced by reflecting the first order diffraction beams on the surface of a reflective phase object under observation to be passed therethrough;

a second hologram located on the focal plane of the second collimator lens and produced by using interference fringes resulting from the interaction between a second reference beam and each of the first order diffraction beams which are reproduced by illumination of the first hologram with a beam equivalent to the first reference beam and passed through the collimator lenses;

at least a third collimator lens located behind the second hologram; and an observation plane located behind the third collimator lens;

whereby the object can be observed by slightly inclining the object for imparting a phase difference to the first order diffraction beam reproduced by illumination of the second hologram with the object beams reflected on the surface of the object, so that a visible image is provided having a three-dimensional illusion on the observation plane.

9. A holographic shearing contrast interferometer according to claim 8, wherein pinhole filters for eliminating diffraction noises are respectively disposed in the focal plane of the objective lens and the focal plane of the third collimator lens.

* * * * *